US008215398B2

(12) United States Patent
Kesavan et al.

(10) Patent No.: US 8,215,398 B2
(45) Date of Patent: Jul. 10, 2012

(54) POLYSACCHARIDE BASED SCALE INHIBITOR

(75) Inventors: Subramanian Kesavan, East Windsor, NJ (US); Gary Woodward, Northwich (GB); Floryan Decampo, Shanghai (CN)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 12/151,560

(22) Filed: Jul. 7, 2008

(65) Prior Publication Data

US 2008/0277620 A1 Nov. 13, 2008

Related U.S. Application Data

(60) Provisional application No. 60/928,169, filed on May 8, 2007.

(51) Int. Cl.
*E21B 21/00* (2006.01)
(52) U.S. Cl. ........ 166/311; 166/279; 166/300; 252/175; 510/108; 510/109; 510/401
(58) Field of Classification Search .................. 252/175; 166/275, 279, 300, 311; 510/108, 109, 401
See application file for complete search history.

(56) References Cited

U.S. PATENT DOCUMENTS

| 4,561,982 | A | 12/1985 | Kuriyama et al. | 210/698 |
| 4,766,959 | A | 8/1988 | Allison | 166/295 |
| 5,548,036 | A | 8/1996 | Kroner et al. | 525/419 |
| 6,488,091 | B1 | 12/2002 | Weaver et al. | 166/300 |
| 6,613,899 | B1 | 9/2003 | Kuzee et al. | 536/124 |
| 6,767,989 | B2 | 7/2004 | Davis et al. | 528/398 |
| 6,814,885 | B2 | 11/2004 | Woodward et al. | 252/180 |
| 6,884,884 | B2 | 4/2005 | Magallanes et al. | 536/114 |
| 2006/0162928 | A1 | 7/2006 | Collins et al. | 166/279 |
| 2007/0015678 | A1 | 1/2007 | Rodrigues et al. | 510/320 |

OTHER PUBLICATIONS

Guar Gum, http://www1.lsbu.ac.uk/water/hygua.html.*
Douglas I. Bain et al "Scale and Corrosion Inhibition by Thermal Polyaspartates", Corrosion/99 paper 120, NACE 1999.
N. Kohler et el "Green Inhibitors for Squeeze Treatments: A Promising Alternative", Corrosion/04 paper 4537, NACE 2004.

* cited by examiner

*Primary Examiner* — Mark Kopec
*Assistant Examiner* — Haidung Nguyen
(74) *Attorney, Agent, or Firm* — Hunton & Williams, LLP

(57) ABSTRACT

A depolymerized-carboxyalkyl polysaccharide formed by depolymerizing a polysaccharide having from 0.5 to 3.0 degrees of substitution and reducing the molecular weight of said polysaccharide before or after said depolymerizing provides a biodegradable scale inhibitor useful to prevent deposition of scale comprising, for example, calcium, barium, sulfate and salts thereof. The depolymerized carboxyalkyl polysaccharide is particularly useful in off shore oil production squeeze treatments and in the treatment of scale formed in industrial water treatment.

27 Claims, 3 Drawing Sheets

% Inhibition of calcium carbonate vs. Mw of guar 1.6 DS

% Inhibition of calcium carbonate vs. Mw of guar 1.6 DS

% Inhibition of calcium carbonate vs. Mw of guar 1.6 DS at 10ppm active

POLYSACCHARIDE BASED SCALE INHIBITOR

CROSS REFERENCE TO RELATED APPLICATIONS

This application claims priority from U.S. Provisional Patent Application Ser. No. 60/928,169, filed May 8, 2007.

FIELD OF THE INVENTION

This invention relates to scale and corrosion inhibitors for use in the prevention of scale on equipment that is exposed to water. The present invention will be described herein with particular reference to a composition and method for preventing scale and corrosion during oil extraction. Even more particularly the present invention relates to a composition, process of making said composition, and a method useful for squeeze treatment of oil wells in oilfield applications.

BACKGROUND OF THE INVENTION

Scaling is a problem that is commonly encountered wherever minerals are dissolved in water. It is a serious problem in aqueous systems, such as cooling water systems; water purification systems; boilers; desalination plants; gas scrubbing; steam generators; dishware and hard surface cleaning; gas and oil production processes, such as topside and downhole applications, sub-sea flow lines, umbilical lines, capillary strings, gravel packs, functional fluids used in oil production; paper processing; sugar refining; mining (heap leaching); and geothermal wells.

In the case of industrial water treatment, such as cooling systems and boilers, the formation of scale is dependent on the characteristics of the water, such as, hardness, pH, temperature and the concentration. In these systems stability to oxidizing biocides, such as bleach (sodium hypochlorite/hypobromite), is very important. In addition, because the cooling water reaches the environment, generally via streams, rivers, oceans and other waterways, the environmental profile of scale inhibitors has becoming increasingly regulated.

In oilfield production, water is heavily used in the oil extraction systems. For example, the water is injected under pressure into an oil reservoir that contains what is generally known as formation water. The pressurized water forces subsurface oil and formation water into nearby production wells. Formation water is usually hard water that contains various scale forming polyvalent metal cations, such as barium, calcium and magnesium. Under certain conditions these metal ions form insoluble salt deposits or scale in processing equipment n.

For offshore oil or gas production, seawater is often used as the injection water for extracting oil. Seawater contains sulfate and carbonate anions. When seawater and formation water come together, the sulfate or carbonate for example from seawater reacts with barium and/or calcium formation water to form insoluble salts, such as barium sulfate, calcium sulfate and calcium carbonate. The insoluble salt deposits or scale readily form on pipes and other production equipment. Sometimes, the formation water may also contain radioactive materials that are incorporated in the scale.

Scale formation can be mitigated or controlled by several methods. For example, calcium carbonate scale can be treated by adding an acid or $CO_2$. However, acid addition can cause increased corrosion and large quantities of acid may be needed to lower the pH sufficiently. As such, this process may be economically unattractive. Equipment can be periodically chemically or mechanically cleaned to remove scale.

The formation of deposits can be prevented by the use of chemical compounds referred to as "scale inhibitors." Scale inhibitors are substances that significantly reduce the formation of scale, partly by inhibiting crystallization and/or retarding the growth of scale forming minerals when applied in sub-stoichiometric amounts. Currently, scale is often treated by the addition of sub stoichiometric levels of water soluble organic scale inhibitors in the 1-500 ppm dosage range. These scale inhibitors are often referred to as threshold scale inhibitors, i.e. there is a threshold dose level below which they do not inhibit scale formation. This limit is often referred to as the minimum inhibitor concentration (MIC).

In order to deliver a required scale inhibitor into an oil production well a squeeze treatment is often performed. This is a method in which a scale inhibitor solution is pumped directly into a formation, often via the production well. An over flush of sea water is used to push the inhibitor further into the formation and into the region around a production well. When oil is subsequently produced, scale inhibitor is released into the water which is produced with the oil.

Clearly some degree of adsorption onto the formation rocks is required so that the inhibitor is released slowly. Inhibitors used in oilfield applications must be stable downhole to high temperatures and they must be compatible with seawater and the formation water present in the oil formation. The lifetime of the squeeze treatment is the time that it takes for the inhibitor in the produced water to drop below the MIC. Any produced water is either re-injected or eventually reaches the environment, so the environmental profile of the inhibitor is very important and there is a growing need for biodegradable scale inhibitors.

Well known organic scale inhibitors, used in multiple applications, are typically polymeric e.g. polyacrylates, polymaleates, poly sulfonates, or small molecules, such as phosphonates and bisphosphonates.

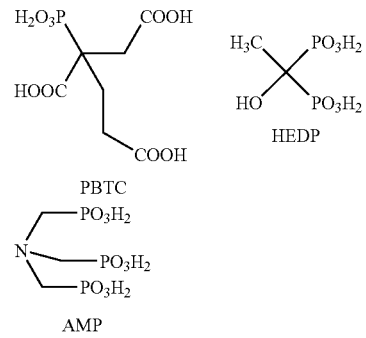

These products are not readily biodegradable and as environmental concerns become more important chemicals such as scale inhibitors, are increasingly scrutinized and legislated. Currently, preferred phosphonates and bisphosphonates include PBTC, HEDP, AMP and diethylenetriamine methylene pentaphosphonate.

One drawback to the polymers and phosphonates described hereinabove is that they are not readily biodegradable. They generally are less than 60% biodegradable in 30 days. Furthermore, the currently available HEDP and AMP phosphonates based products are not stable against oxidizing biocides such as bleach.

There have been several attempts to provide improved "eco-friendly" or environmentally safe biodegradable scale inhibitors. Well known industrial eco-friendly scale inhibitors, include various polyaspartates and inulin.

Bain, Fan, Fan and Ross describe a thermal polyaspartate for use as a biodegradable scale inhibitor. (D. Bain, G. Fan, J. Fan and R. Ross "Scale and Corrosion Inhibition by Thermal Polyaspartates", Corrosion/99 paper 120, NACE 1999). However, the proposed thermal polyaspartate does not perform well, particularly under severe scaling conditions such as that of production wells.

Kohler, Bazin, Zaitoun and Johnson propose the use of certain Polyaspartates or Carboxy Methyl Inulin (CMI) as a biodegradable scale inhibitor. (N. Kohler, B. Bazin, A. Zaitoun, T. Johnson "Green Inhibitors for Squeeze Treatments: A Promising Alternative", Corrosion/04 paper 4537, NACE 2004) However, the proposed CMI and polyaspartates do not work as well as other non-biodegradable inhibitors and neither product is fully biodegradable.

Overall, the known polyaspartates and inulin are not highly active and require huge doses to perform at an acceptable level. Accordingly these known polyaspartates and inulin are not very cost effective when compared to current non-biodegradable products. Thus, there is a widely-recognized need in the oilfield and water treatment industries for new cost effective biodegradable scale inhibitors, capable of operating under severe scaling conditions.

A common practical problem is that such biodegradable inhibitors do not exhibit sufficient thermal stability in use. Even where scale inhibitors are highly cost-effective, further constraints are imposed by the need for them to be thermally and hydrolytically stable, safe for operators to use, environmental friendly and compatible with high levels of scaling cations and other chemicals that may be added to the system, such as corrosion inhibitors, both non-oxidizing and oxidizing biocides and demulsifiers.

SUMMARY OF THE INVENTION

In one aspect, the present invention is a method of manufacturing a depolymerized carboxyl alkyl guar having a degree of substitution of up to 3 carboxylic groups per sugar unit for use as a scale inhibitor In another aspect, the present invention is a modified polysaccharide that is effective at inhibiting various scale formations. In still yet another aspect, the invention is a method of manufacturing a polysaccharide based scale inhibitor by selecting an optimal molecular weight and degree of substitution range for scale inhibition to.

In another aspect, the invention is a method of manufacturing a polysaccharide based scale inhibitor comprising the steps of varying the degree of substitution and reducing the molecular weight of a polysaccharide via oxidation, enzyme reduction, acid reduction, ionizing radiation, or electronic beam radiation, whereby one or more carboxyalkyl groups is formed on said polysaccharide before or after reducing said molecular weight.

In yet another aspect, the invention is a polysaccharide based scale inhibitor comprising a polysaccharide having a substitution between 0.5 and 3.0 and a molecular weight up to 500,000

The present invention in yet another aspect is a biodegradable polysaccharide based scale inhibitor whereby said scale inhibitor is stable under various temperatures.

There is also provided a method for inhibiting scale in a production well comprising injecting down a well an aqueous fluid comprising a biodegradable polysaccharide having a degree of substitution between 0.5 and 3.0 and a molecular weight up to 500,000; wherein adding an effective amount biodegradable polysaccharide prevents or reduces scale in said production well.

It is a further object of this invention to provide a biodegradable scale inhibitor having improved scale removal at high temperatures.

It is still another object of the present invention to provide a scale inhibitor that can be formulated with a relatively low level of a biodegradable polysaccharide for cost-effective performance.

It is a further object of the present invention to provide methods of treating scale or corrosion in subterranean wells comprising the steps of first squeezing a biodegradable polysaccharide scale inhibitor of the invention into a reservoir section surrounding a well and second recycling said scale inhibitor through the well with formation fluids.

Another object of the invention is to provide a scale inhibitor comprising a biodegradable polysaccharide having a high tolerance to organic/inorganic salts, such as KCl, tetramethyl ammonium chloride (TMAC), $Ca^{2+}$ and $Mg^{2+}$ ions.

Yet another object of the invention is to provide a biodegradable polysaccharide based scale inhibitor that is stable against oxidizing biocides such as bleach.

Still yet another object of the invention is to provide a biodegradable polysaccharide based scale inhibitor that is thermally and hydrolytically stable.

Still another object of the invention is to provide a polysaccharide based biodegradable scale inhibitor effective in severe scaling conditions.

These and other objects of the invention will readily be apparent to those skilled in the art as reference is made to the detailed description of the preferred embodiment.

DETAILED DESCRIPTION OF THE INVENTION

Figure 1:
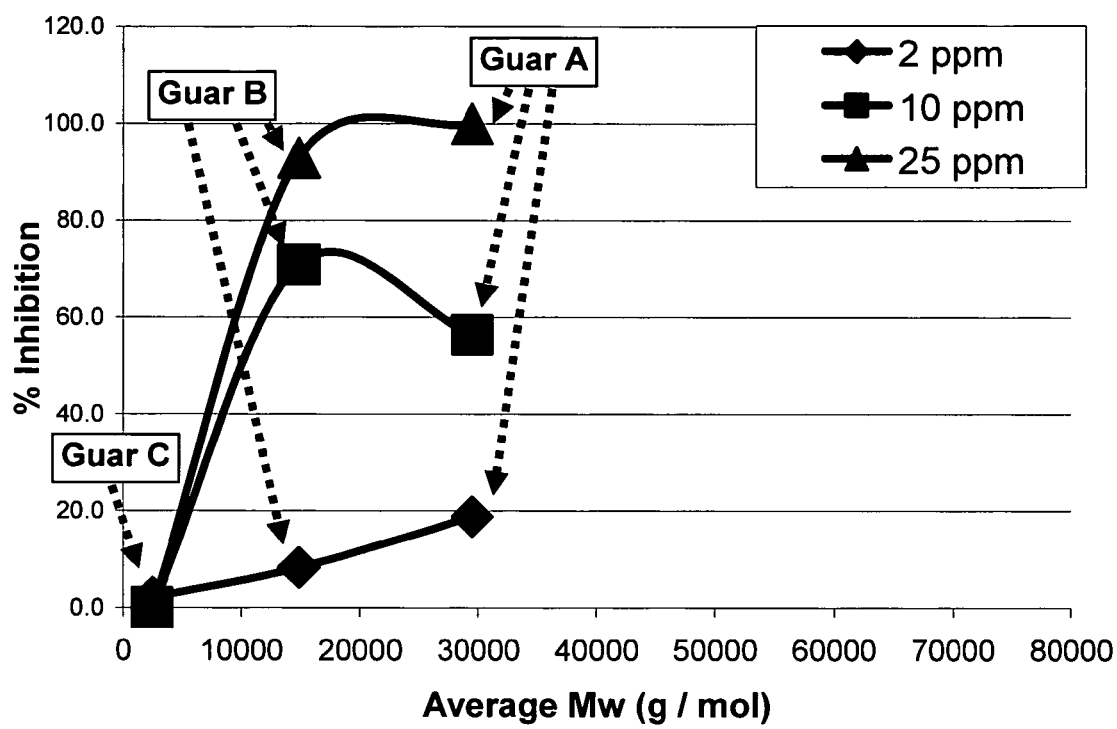
FIG. 1 is a graph showing the percentage inhibition of calcium carbonate versus the weight average molecular weight of guar 1.6 DS.

The present invention concerns novel functionalized polysaccharide based scale inhibitors comprising depolymerized carboxyalkyl polysaccharides from 0.5 to 3 carboxylic groups per sugar unit formed by a process of depolymerizing a polysaccharide, particularly a carboxyalkyl polysaccharide. The polysaccharide may be further derivatized with alkylcarboxy groups after the molecular weight has been reduced.

Preferred polysaccharides in accordance with the invention are derivatized polygalactomannans. More preferably the polysaccharides in accordance with the invention are carboxyalkyl derivatized polygalactomannans having a degree of substitution of between about 0.5 and about 3.0. Particular levels of degree of substitution may be preferred for particular scales and applications.

As used herein, the term "degree of substitution" means the average substitution of functional groups per anhydro sugar unit in the polygalactomannan gums. In guar gum, the basic unit of the polymer consists of two mannose units with a glycosidic linkage and a galactose unit attached to a hydroxyl group of one of the mannose units. On the average, each of the anhydro sugar units contains three available hydroxyl sites. A degree of substitution of three would mean that all of the available hydroxyl sites have been esterified with functional groups. A particularly preferred functional group is the carboxymethyl group. Good results have been obtained with starting materials having a degree of substitution of between about 0.5 and about 3.0. and more preferably, materials having a degree of substitution ranging from about 0.5 to about 2.0.

In one embodiment of the invention a preferred derivatized polygalactomannan has a general formula (I):

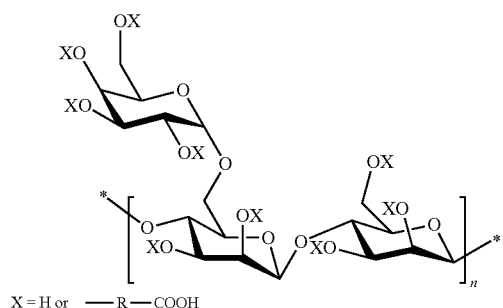

X = H or —R—COOH wherein a degree of substitution of 3 would refer to all three X groups per ring being derivatized. R is preferably $C_1$-$C_{22}$ linear, branched or substituted alkyl, with hetero atoms such as, for example, amine, carboxy, ether, alcohol or thio functionalities. Alternatively, R may be $C_1$ to $C_{22}$ aryl or $C_1$ to $C_{22}$ substituted aryl group.

Polygalactomannans are naturally occurring polysaccharides composed principally of galactose and mannose units and are usually found in the endosperm of leguminous seeds, such as guar, locust bean, honey locust, flame tree, and the like. Guar flour, for example, is composed mostly of a galactomannan that is essentially a straight chain mannan with single membered galactose branches. The mannose units are linked in a 1-4-.beta.-glycosidic linkage and the galactose branching takes place by means of a 1-6 linkage on mannose units in an irregular manner. The ratio of galactose to mannose in the guar polymer is about one to two.

As will be known to those skilled in the art, the guar endosperm is commonly referred to as "purified splits", "double purified splits" or "triple purified splits" depending upon the degree of purification. "Purified splits" are obtained by mechanical separation of the endosperm from the hull and germ of the guar seed in as pure and intact a form as possible with no other processing steps. Repeating the process produces double purified splits. Repeating the process again produces triple purified splits. Splits are then ground into guar powder. Preferred forms of carboxyalkyl polysaccharide include raw splits, powder or solution.

Locust bean gum is also a polygalactomannan gum of similar molecular structure in which the ratio of galactose to mannose is one to four. Guar and locust bean gum are the preferred sources of the polygalactomannans, principally because of the commercial availability thereof.

In use the polygalactomannan may be either in its natural state (i.e., pure guar gum or locust bean gum) or may be derivatized. Derivatized polygalactomannans include one or more non-ionic and/or ionic groups. Examples of the types of functional groups involved in producing the derivatives include hydroxyalkyl groups, carboxyl group, carboxyalkyl groups, quaternary ammonium groups, sulfonate groups, cyanoalkyl groups, phosphate groups, siloxane groups and the like having varying degrees of substitution and molecular substitution. Specific examples of such polygalactomannans, include hydroxypropyl guar, hydroxyethyl guar, carboxymethyl guar, carboxymethyl hydroxypropyl guar, guar hydroxypropyltrimonium chloride and the like having varying degrees of substitution and molar substitution. Such derivatized polygalactomannans are sold by Rhodia, Inc. under the trade names Jaguar 8000, Jaguar 8710 and Jaguar 8600. Many commercially available starting guar materials may contain small amounts of additives such as borax, glyoxal and the like. These starting materials are expressly intended to constitute part of the present invention.

Alternative polysaccharide materials which may be selected as the starting material include starches, celluloses and xanthan gum. Examples of starches include both natural and modified starches, such as dextrinated, hydrolyzed, oxidized, cross-linked, alkylated, hydroxyalkylated, acetylated, or fractionated (e.g., amylose and amylopectin). The starch may be of any origin, for example, corn starch, wheat starch, potato starch, tapioca starch, sago starch, rice starch, waxy corn starch or high-amylose corn starch.

Examples of celluloses include hydroxyethyl cellulose, hydroxypropyl cellulose, cellulose gum, carboxymethyl cellulose and alkyl celluloses. Similar to the polygalactomannans, these derivatized materials may have a degree of substitution and/or molar substitution ranging from about 0.0 to about 3.0.

Still other polysaccharides which may be selected as a starting material include polydextrose, chitin/chitosan and derivatives thereof, alginate compositions, carageenan gum, pectin, gum karaya and gum arabic.

The depolymerized carboxyalkyl polysaccharide may be manufactured in a single or multi step process comprising of at least one derivitization stage and one depolymerization stage. The present invention is not limited to any particular order or number of processing steps, the depolymerization and carboxyalkylation steps can be carried out concurrently. Depolymerization can be carried out using any suitable depolymerization process as is well know in the art. Depolymerization may occur using solution or carboxyalkyl polysaccharide powder or in the case of underivatized polysaccharide also on the raw polysaccharide splits. For example depolymerization may also be performed by spraying hydrogen peroxide or other oxidizers on carboxyalkyl polysaccharide powder, as shown in U.S. Pat. No. 6,884,884 by Jesse Magallanes et al. assigned to Rhodia, Inc. and which is herein incorporated by reference in its entirety.

Further examples of depolymerization methods to reduce the molecular weight include, by radiation (including ionizing, ultraviolet and electron beam), chemical (including acids and oxidized hydrogen peroxide) or enzyme reduction. The present invention is not limited to these methods.

In a preferred embodiment of the invention the molecular weight of the carboxyalkyl polysaccharide is reduced by heating the polysaccharide in the presence of hydrogen peroxide.

The applicants have discovered that there is a range of molecular weight and degree of substitution which may be determined to achieve optimum performance as an effective scale inhibitor. The method of the invention allows for independent control of the molecular weight and the degree of substitution. Experiments have shown that for barium sulfate scale inhibition there is optimum performance obtained with a degree of substitution of 1.6 and a weight average molecular weight range around or below 500,000.

The depolymerized carboxyalkyl polysaccharides of the invention are effective for the inhibition of scale caused by metal carbonates and basic carbonates, particularly those of metals of Group IIA of the Periodic Classification, as well as scale caused by carboxylate, fluoride, hydroxide, phosphate, phosphonate, silicate and sulfate. $BaSO_4$, $SrSO_4$, $SrCO_3$, $CaCO_3$, $Mg(OH)_2$, $CaSO_4$, $CaF_2$, ZnS, FeS, PbS, NaCl, calcium phosphate, silicate, silica, Scale inhibitors of the invention may be useful in aqueous based functional fluids such as hydraulic fluids, lubricants, cutting fluids and oilfield drilling mud.

In particular, the depolymerized carboxyalkyl polysaccharides of the invention may be used in squeeze treatments. They are especially effective in preventing barium sulfate scale. For example, in oil extraction the pipe or well is typically flushed out with aqueous surfactant to provide a water wettable surface and then impregnated with a solution comprising an inhibitor. The calcium salt may be formed in situ either by calcium in the deposits where the latter comprises limestone, or by prior or subsequent treatment of the pipe or well with an aqueous calcium salt, for example, where the deposits comprise sandstone.

Effective concentrations of oxidized carboxyalkyl polysaccharides may typically range from 1 to 500 ppm, preferably 1.5 to 20 ppm, and more preferably 2 to 10 ppm. For oilfield scale prevention where barium sulfate is a problem, concentrations in the range 5 to 200 ppm, preferably 8 to 25 ppm, and more preferably 10 to 20 ppm are optimal.

Depolymerized carboxyalkyl polysaccharides scale inhibitors according to the invention may be used in combination with one another or in conjunction with other water treatment agents, including surfactants, such as anionic surfactants (for example, $C_{10-20}$ alkyl benzene sulphonates, $C_{10-20}$ olefin sulphonates, $C_{10-20}$ alkyl sulfates, $C_{10-20}$ alkyl 1 to 25 mole ether sulfates, $C_{10-20}$ paraffin sulphonates, $C_{10-20}$ soaps, $C_{10-20}$ alkyl phenol sulfates, sulphosuccinates, sulphosuccinamates, lignin sulphonates, fatty ester sulphonates, $C_{10-20}$ alkyl phenol ether sulfates, $C_{10-20}$ alkyl ethanolamide sulfates, $C_{10-20}$ alpha sulphofatty acid salts, $C_{10-20}$ acyl sarcosinates, isethionates, $C_{10-20}$ acyl taurides, $C_{10-20}$ alkyl hydrogen phosphates); non-ionic surfactants (for example, ethoxylated material or synthetic C.sub.8-25 alcohols, ethoxylated fatty acids, ethoxyl/propyleneoxy block copolymers, ethoxylated fatty amines, mono- and di-alkanolamides, amine oxides and $C_{10-20}$ acyl sorbitan and/or glyceryl ethoxylates); amphoteric surfactants (for example, betaines, sulphobetaines, and/or quaternized imidazoline); or cationic surfactants (for example, benzalkonium salts, $C_{10-20}$ alkyl trimethyl ammonium salts, and/or $C_{10-20}$ alkyl trimethyl or tris (hydroxymethyl) phosphonium salts); sequestrants, chelating agents, corrosion inhibitors and/or other threshold agents (for example, sodium tripolyphosphate, sodium ethylenediamine tetracetate, sodium nitrilo triacetate, tetra potassium pyrophosphate, acetodiphosphonic acid and its salts, ammonium trismethylene phosphonic acid and its salts, ethylenediamine tetrakis (methylene phosphonic) acid and its salts, diethylenetriamine pentakis (methylene phosphonic) acid, hexamethylenediamine tetrakis (methylene phosphonic) acid, bishexamethylenetriamine pentakis (methylene phosphonic) acid and ethanolamine bis(methylenephosphonic) acid and its salts); tolyltriazole and mixtures of nitrate, benzoate, HHP and/or PTCB) biocides (for example, tetrakis (hydroxymethyl) phosphonium salts, formaldehyde glutaraldehyde); oxidizing biocides and/or bleaches (for example, chlorine, chlorine dioxide, hydrogen peroxide, sodium perborate; foam controlling agents such as silicone antifoams, acetylenic diols; oxygen scavengers such as hydrazines and/or hydroxylamines; pH controlling and/or buffering agents such as amines, borates citrates and/or acetates; chromium salts; zinc salts; or other water treatment agents such as polymeric dispersants and coagulants including polymaleic, polyacrylic acids, and polyvinylsulphonic acids, polyacrylic acid salts, and polyvinylsulphonic acid salts, starches and/or carboxy methyl cellulose and molybdates.

The invention provides formulations comprising an effective amount of a depolymerized carboxyalkyl polysaccharide of the invention and any of the aforesaid known water treatment agents. Such formulations may, for example, contain from 5 to 95% by weight of a depolymerized carboxyalkyl polysaccharide of the invention and from 5 to 90% by weight of one or more of any of the aforesaid water treatment agents.

Scale inhibitors according to the present invention have been found to be particularly effective for scale inhibition in water containing upwards of 4000 ppm alkaline earth metal ions, generally expressed as ppm calcium carbonate. The present invention also provides a method of treating water, said method comprising the addition thereto of an effective amount of an inhibitor according to the present invention, as hereinbefore described.

The water may be, for example, cooling water, oilfield water, water used in paper manufacture, water in a hydraulic system, water in a desalination system (including membrane process and evaporative process desalination systems), boiler water, geothermal water or water in an irrigation system.

Not only is the depolymerized carboxyalkyl polysaccharides scale inhibitor of the invention superior in terms of cost because of its use of inexpensive polysaccharides and oxidizing agents as well as the ease of performing depolymerization and molecular weight reduction, but it is also highly effective against a broad variety of scale. The depolymerized carboxyalkyl polysaccharides of the invention also exhibit excellent stability characteristics, particularly thermal stability. Under optimum conditions of use, the inhibitors according to the present invention are biodegradable and environmentally safe.

The invention is illustrated by the following non-limiting examples.

EXAMPLES

Example I

Depolymerization of Carboxymethyl Guar

Depolymerization of Carboxymethyl Guar 1.6 DS
Procedure

A 10% solution of carboxymethyl guar (commercial grade Meyprogum R-600 from Danisco) was prepared using 2% potassium chloride solution. Meyprogum R-600 is a high substituted carboxymethyl guar with a degree of substitution (DS) of 1.6. The guar solution was then mixed with different amounts of 30% $H_2O_2$ and placed in an oven at 66° C. (150° F.) for 3 to 24 h. Such a treatment allows depolymerizing the guar polymer to different extent by oxidative cleavage. The conditions used to prepare three different depolymerized guar samples are summarized in Table 1.

TABLE 1

Depolymerization conditions of Meyprogum R-600-Guar 1.6 DS

|  | Guar A | Guar B | Guar C | Guar D (control) |
|---|---|---|---|---|
| Meyprogum R-600 | 11 g | 10 g | 10 g | 5 g |
| 2% KCl solution | 97 g | 80 g | 60 g | 102 g |
| 30% $H_2O_2$ | 3 g | 10 g | 30 g | NA |
| Time (h) | 24 | 24 | 3 | NA |

Analyses

The samples were dissolved in the mobile phase at 0.5% by weight and filtered through 0.45 µm PVDF filters prior to injection. Polyethylene glycol standards ranging from 194 to 22,000 Da were used for calibration. The following conditions were used to measure the molecular weight (Mw) of the various guar samples:

| | |
|---|---|
| Column: | Waters Ultrahydrogel 250 and 250 (X2) in series |
| Mobile Phase: | 100 mM $NaNO_3$, 0.02% $NaN_3$ |
| Flow Rate: | 1.0 ml/min |
| Detectors: | Agilent RI detector |
| Inj. Volume: | 100 µl |
| Temperature: | ambient |
| Run time: | 45 minutes |

The Mw distributions obtained for the guar samples are summarized in Table 2.

TABLE 2

Mw Distributions

| Sample | Peak MW $M_p$ | Wt. Avg. $M_w$ | No. Avg. $M_n$ | Polydispersity $M_w/M_n$ |
|---|---|---|---|---|
| Guar A | 33,400 | 29,500 | 18,100 | 1.63 |
| Guar B | 16,600 | 14,900 | 9,820 | 1.51 |
| Guar C | 1,620 | 2,480 | 2,130 | 1.16 |
| Guar D | 1,420,000 | 1,290,000 | 777,000 | 1.66 |

Scale Inhibition
Calcium Carbonate
Method:

The performance for calcium carbonate scale inhibition was measured by using the protocol described in NACE test method TM-0374-2001. The dosage of the various guar samples was based on the active ingredient Meyprogum R-600.

A brief description of the NACE test method TM-0374-2001 is given below. Please refer to the NACE test method TM-0374-2001 for complete details.

Two synthetic brines, one calcium containing brine and one bicarbonate containing brine are prepared in deionized water as follows and then saturated with carbon dioxide by bubbling $CO_2$ gas through them. Then, equal amounts by volume of the two brines are mixed together in a test cell along with the required amount of the scale inhibitor and capped immediately. Then it is placed in an oven at 71° C. for 24 hours. The sample is removed from the oven and allowed to cool to 25° C. Without mixing the sample, a small amount of the liquid is taken without any calcium carbonate crystals and analyzed for calcium and compared with a sample without inhibitor to determine the extent of inhibition.

Calcium Containing Brine

| Salt | M (Salt) | % mass | Ion Conc. (g/L) | conc. (mol/L) | Salt (g/L) | Salt (g/2 L) |
|---|---|---|---|---|---|---|
| NaCl | 58.5 | 1.297 | 12.974 | 0.564 | 33.000 | 66.000 |
| CaCl2, 2H2O | 147.1 | 0.331 | 3.312 | 0.083 | 12.150 | 24.300 |
| MgCl2, 6H2O | 203.3 | 0.044 | 0.440 | 0.018 | 3.680 | 7.360 |

Bicarbonate Brine

| Salt | M (Salt) | % mass | Ion Conc. (g/L) | conc. (mol/L) | Salt (g/L) | Salt (g/2 L) |
|---|---|---|---|---|---|---|
| NaCl | 58.5 | 1.297 | 12.974 | 0.564 | 33.000 | 66.000 |
| NaHCO3 | 84 | 0.534 | 5.345 | 0.088 | 7.36 | 14.72 |

Results:
1.6 DS Guars

The results obtained with the guar samples at 2, 10, 25, 100 and 250 ppm (active ingredient) are summarized in Table 3. It clearly appears that Guar A and B were superior to Guar C and D since they provided a complete inhibition down to 25 ppm. Based on these results, the minimum inhibitory concentration (MIC) of Guar A and B should be between 10 and 25 ppm. Guar C and D are completely ineffective up to 25 ppm and guar C only provide 38% inhibition when dosed at 250 ppm.

TABLE 3

Calcium carbonate inhibition results

% Inhibition of calcium carbonate

| Dosage (ppm) | Guar A | Guar B | Guar C | Guar D |
|---|---|---|---|---|
| 2 | 18.8 | 8.3 | 2.1 | 0 |
| 10 | 56.3 | 70.8 | 0 | 0 |
| 25 | 100 | 92.9 | 0 | 0 |
| 100 | 100 | 100 | 28.6 | Not run |
| 250 | 97.6 | 100 | 38.1 | Not run |

FIG. 1 shows the inhibition results plotted versus the Mw corresponding to the four guar samples. This graph shows that low (Guar C) and high (Guar D) Mw samples did not provide any inhibition for concentrations of 25 ppm and lower. On the contrary, Mw of 15,000 (Guar B) and 30,000 (Guar A) provided 100% inhibition at 25 ppm. Based on these results, it appears that the activity of the Guar is correlated to the Mw. In this case, with a degree of substitution of 1.6 it appears that the performance of the Guar is optimum for Mw between 8,000 and 50,000.

To confirm these results two more experiments were carried out at 10 ppm active which is the ideal concentration to differentiate the performance between the candidates. In Table 4 are summarized the results obtained at 10 ppm active for the 1.6 DS guars.

TABLE 4

Calcium carbonate inhibition results at 10 ppm active

% Inhibition of calcium carbonate

| Run | Guar A | Guar B | Guar C |
|---|---|---|---|
| 1 | 56.3 | 70.8 | 0 |
| 2 | 42.4 | 69.7 | 0 |
| 3 | 63.6 | 86.4 | 4.5 |
| Average | 54.1 | 75.6 | 1.5 |

Figure 2:
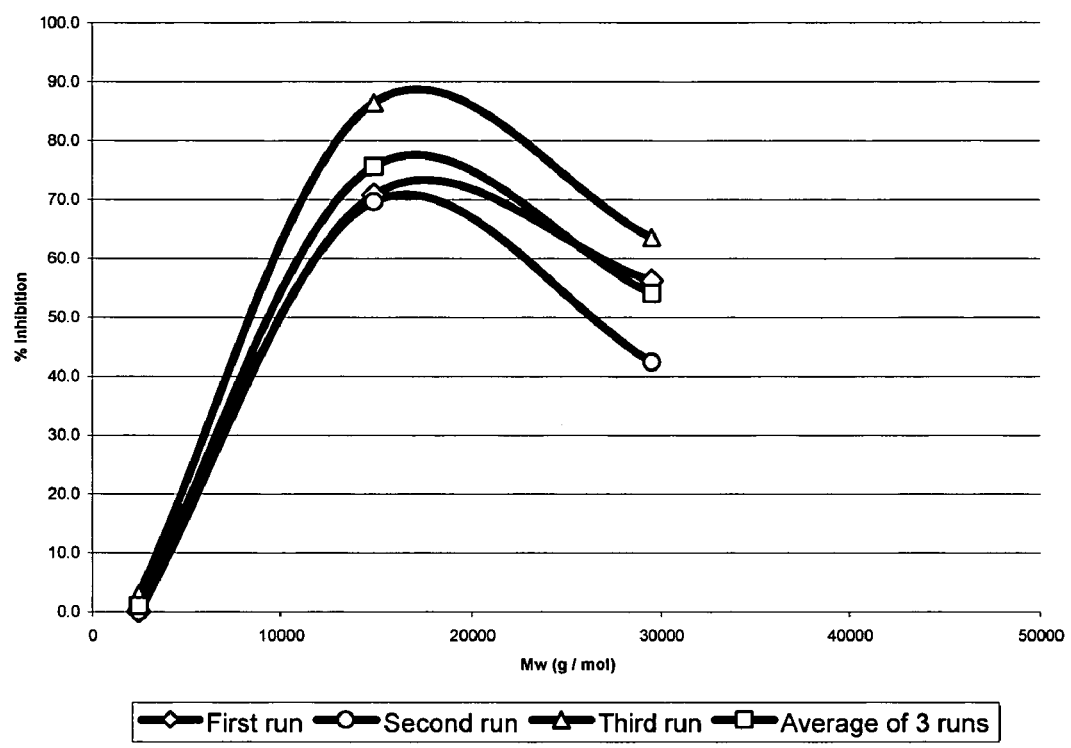
FIG. 2 is a graph showing the percentage inhibition of calcium carbonate versus the weight average molecular weight of guar 1.6 DS at 10 ppm for different runs.

FIG. 2 shows the % inhibition plotted versus the Mw for the different runs and the average value. It clearly appears that the same behavior is observed for the different runs.

Example II

Barium sulfate

Method:

Seawater and Formation water are prepared as shown in Table 5 and 6.

TABLE 5

Formation water composition

| Salt | Ion | ppm | Salt (g/L) |
|---|---|---|---|
| NaCl | $Na^+$ | 31275 | 79.50 |
| CaCl2,2H2O | $Ca^{2+}$ | 2000 | 7.34 |
| MgCl2,6H2O | $Mg^{2+}$ | 739 | 6.18 |
| KCl | $K^+$ | 654 | 1.25 |
| BaCl2,2H2O | $Ba^{2+}$ | 269 | 0.48 |
| SrCl2,6H2O | $Sr^{2+}$ | 87.6 | 2.35 |

TABLE 6

Seawater composition

| Salt | Ion | ppm | Salt (g/L) |
| --- | --- | --- | --- |
| NaCl | $Na^+$ | 10890 | 27.7 |
| CaCl2,2H2O | $Ca^{2+}$ | 428 | 1.57 |
| MgCl2,6H2O | $Mg^{2+}$ | 1368 | 11.44 |
| KCl | $K^+$ | 460 | 0.88 |
| BaCl2,2H2O | $Ba^{2+}$ | 0 | 0.00 |
| SrCl2,6H2O | $Sr^{2+}$ | 0 | 0.00 |
| Na2SO4 anhydrous | $SO_4^{2-}$ | 2690 | 3.98 |

Inhibitors solutions of a 10,000 ppm were made up in DI water in 100 ml volumetric flask. 50 ml of seawater were transferred into a plastic bottle along with the appropriate amount of inhibitor solution (0.3 or 0.15 mL). A blank and a control were also prepared. The blank was made of 50 ml of seawater without any inhibitor while the control was made of 50 ml of DI water. In as many 125 mls plastic bottles as bottles of inhibitor stock solutions, 50 ml of formation water were placed using a measuring cylinder and buffered at pH=5.5 using 1 ml of a sodium acetate/acetic acid buffer (34 g of sodium acetate 3-hydrate and 0.75 g of concentrated acetic acid made up to 250 ml in a volumetric flask with DI water).

All bottles are placed in an oven at 95° C. and left to equilibrate to test temperature (1 h20). Once this temperature was reached, the contents of the seawater/control bottles were poured into the formation water bottles and replaced in the oven at the test temperature. This gave final inhibitor test doses at 5, 7.5 and 15 ppm.

Bottles were sampled after 2 hours. A 1 ml sample was taken from each bottle (taking care not to pick up any deposited scale) with a 1 ml plastic pipette. This was injected into a plastic test tube containing 9 ml of a pre-prepared quench solution (5.71 g of KCl, 1 g of PVSA in DI water, adjusted to pH=8.0-8.5 with NaOH and made up to 1 L in a 1 L volumetric flask). A cap was placed on the test tube and the solution was well mixed. Each sample was analyzed for residual Barium and strontium, by ICP analysis within the 48 hours (digested within 24 h).

The ICP results gave the concentration of each compound in ppm and an appropriate calculation allowed transforming the ppm in percentage efficiency for each scale inhibitor. The BaSO4 efficiency w calculated according to the following equation:

$$\% \text{ efficiency} = \frac{[Ba2+ \text{ in sample}] - [Ba2+]\min}{[Ba^{2+}]_{max} - [Ba^{2+}]_{min}} * 100$$

with [Ba2+]max=Ba2+ content of maximum (FW/H2O) control
[Ba2+]max=Ba2+ content of minimum (FW/SW) blank
Results:
1.6 DS Guars The results obtained with the guar samples at 25 and 250 ppm (active ingredient) are summarized in Table 3. Once again it clearly appears that Guar A and B were superior to Guar C and D.

TABLE 7

Barium sulphate inhibition results

| Guar | Dosage (ppm) | BaSO4 % Inhibition | SrSO4 % Inhibition |
| --- | --- | --- | --- |
| A | 25 | 39.8 | 69.2 |
|   | 50 | 65.7 | 80.8 |
|   | 250 | 100 | 88.8 |

TABLE 7-continued

Barium sulphate inhibition results

| Guar | Dosage (ppm) | BaSO4 % Inhibition | SrSO4 % Inhibition |
| --- | --- | --- | --- |
| B | 25 | 34.3 | 73.1 |
|   | 50 | 59.3 | 87.7 |
|   | 250 | 100 | 87.5 |
| C | 25 | 0 | 0 |
|   | 50 | 0 | 6.2 |
|   | 250 | 0 | 52 |
| D | 25 | 0 | 7.7 |
|   | 50 | 2.8 | 36.9 |
|   | 250 | 13.8 | 40.1 |

Figure 3:
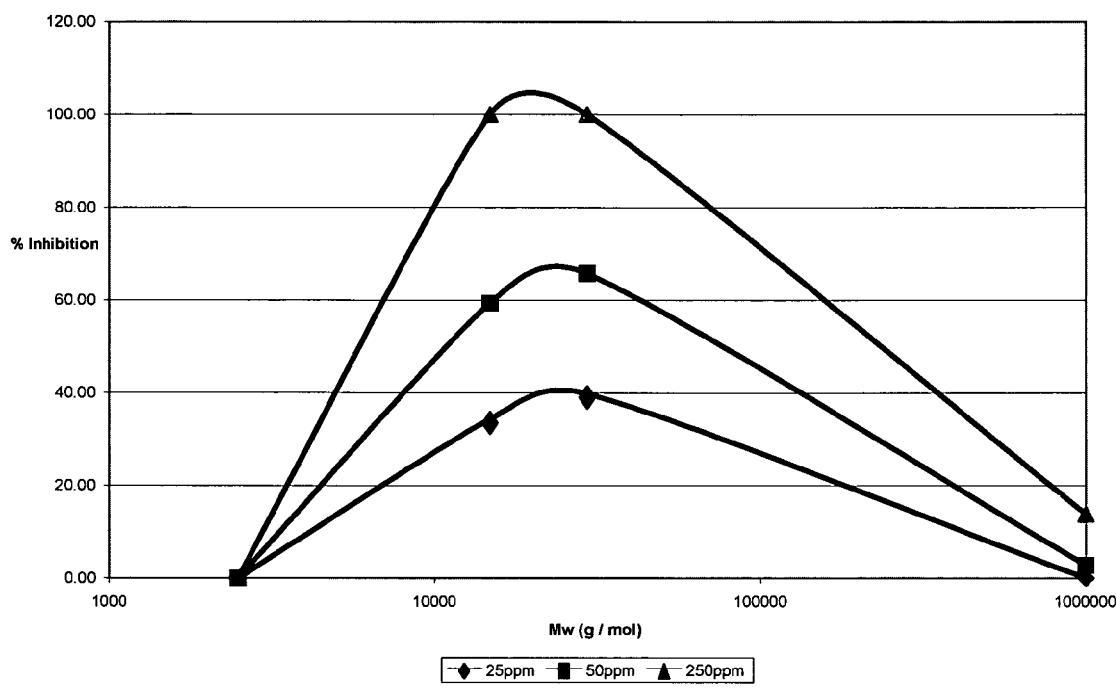
FIG. 3 is a graph showing barium sulfate inhibition after 2 hours versus the weight average molecular weight of guar 1.6 DS.

The results are summarized in FIG. 3.

Example III 50 gm of 0.9 DS carboxymethyl guar (CMG-0.9) was dissolved in 950 gm of 2% potassium chloride solution to make a 5% polymer solution. 100 gm of the 5% polymer solution was put in several jars and depolymerized using different levels of 30% H2O2 by heating in an oven at 75° C. for 24 hours. The amount of peroxide used to depolymerize and the resulting molecular weight are tabulated in Table 8. Each of the samples was tested for calcium carbonate scale inhibition using NACE test method TM-0374-2001 as detailed in example 1 at a CMG-0.9 concentration of 10 ppm. The calcium inhibition results are tabulated in Table 8.

TABLE 8

Scale inhibition as a function of molecular weight for 0.9 DS carboxymethylguar(CMG-0.9)

| Amount of 30% H2O2 added to 100 gm solution | Weight average molecular weight, Mw | % Calcium carbonate inhibition at polymer concentration dosage of 10 ppm |
| --- | --- | --- |
| 0.01 gm | 266,000 | 64 |
| 0.02 gm | 174,000 | 61 |
| 0.05 gm | 83,100 | 74 |
| 0.1 gm | 50,200 | 94 |
| 0.2 gm | 21,600 | 66 |
| 0.5 gm | 8,770 | 64 |
| 1.5 gm | 3,150 | 57 |
| 2.0 gm | 2,340 | 46 |
| 3.0 gm | 1,770 | 7 |

Example IV 50 gm of 2.1 DS carboxymethyl guar (CMG-2.1) was dissolved in 950 gm of 2% potassium chloride solution to make a 5% polymer solution. 100 gm of the 5% polymer solution was put in several jars and depolymerized using different levels of 30% H2O2 by heating in an oven at 75° C. for 24 hours. The amount of peroxide used and the resulting molecular weights are tabulated in Table 9. Each of these samples was tested for calcium carbonate scale inhibition using NACE test method TM-0374-2001 as detailed in example 1 at a CMG-2.1 concentration of 10 ppm. The calcium inhibition results are tabulated in Table 9.

TABLE 9

Scale inhibition of 2.1 DS carboxymethyl guar(CMG-2.1) at different molecular weights

| Amount of 30% H2O2 added to 100 gm of solution | Weight average molecular weight, Mw | % Calcium carbonate inhibition at polymer concentration dosage of 10 ppm |
|---|---|---|
| 0 gm | 130000 | 38 |
| 0.01 gm | 117000 | 40 |
| 0.02 gm | 110000 | 34 |
| 0.05 gm | 94200 | 34 |
| 0.1 gm | 62300 | 60 |
| 0.2 gm | 43700 | 54 |
| 0.5 gm | 21300 | 68 |
| 1.5 gm | 9080 | 78 |

Example V 50 gm of 0.6 DS carboxymethyl guar (CMG-0.6) was dissolved in 950 gm of 2% potassium chloride solution to make a 5% polymer solution. 100 gm of the 5% polymer solution was put in several jars and depolymerized using different levels of 30% H2O2 by heating in an oven at 75° C. for 24 hours. The amount of peroxide used and the resulting molecular weights are tabulated in Table 10. Each of these samples was tested for calcium carbonate scale inhibition using NACE test method TM-0374-2001 as detailed in example 1 at a CMG-0.6 concentration of 10 ppm. The calcium inhibition results are tabulated in Table 10.

TABLE 10

Scale inhibition of 0.6 DS carboxymethyl guar(CMG-0.6) at different molecular weights

| Amount of 30% H2O2 added to 100 gm of solution | Weight average molecular weight, Mw | % Calcium carbonate inhibition at polymer concentration dosage of 10 ppm |
|---|---|---|
| 0.02 gm | 192,000 | 33 |
| 0.05 gm | 100,000 | 38 |
| 0.1 gm | 46,800 | 29 |
| 0.2 gm | 21,800 | 26 |
| 0.5 gm | 8,490 | 0 |
| 1.5 gm | 3,790 | 6 |
| 3.0 gm | 2,680 | 13 |

Example VI 50 gm of 1.6 DS carboxymethyl guar (CMG-1.6) was dissolved in 950 gm of 2% potassium chloride solution to make a 5% polymer solution. 100 gm of the 5% polymer solution was put in several jars and depolymerized using different levels of 30% H2O2 by heating in an oven at 75° C. for 24 hours. The amount of peroxide used and the resulting molecular weights are tabulated in Table 11. Each of these samples was tested for calcium carbonate scale inhibition using NACE test method TM-0374-2001 as detailed in example 1 at a CMG-1.6 concentration of 10 ppm. The calcium inhibition results are tabulated in Table 11.

TABLE 11

Scale inhibition of 1.6 DS carboxymethyl guar(CMG-1.6) at different molecular weights

| Amount of 30% H2O2 added to 100 gm of solution | Weight average molecular weight, Mw | % Calcium carbonate inhibition at polymer concentration dosage of 10 ppm |
|---|---|---|
| 0 gm | 1,080,000 | 33 |
| 0.01 gm | 986,000 | 22 |
| 0.02 gm | 947,000 | 19 |
| 0.05 gm | 629,000 | 23 |
| 0.1 gm | 196,000 | 39 |
| 0.2 gm | 81,600 | 53 |
| 0.5 gm | 25,300 | 88 |
| 1.5 gm | 8,080 | 89 |

Example VII 50 gm of 1.2 DS carboxymethyl cellulose, 12M8 from Aqualon (CMC-1.2) was dissolved in 950 gm of 2% potassium chloride solution to make a 5% polymer solution. 100 gm of the 5% polymer solution was put in several jars and depolymerized using different levels of 30% H2O2 by heating in an oven at 75° C. for 24 hours. The amount of peroxide used and the resulting molecular weights are tabulated in Table 12. Each of these samples was tested for calcium carbonate scale inhibition using NACE test method TM-0374-2001 as detailed in example 1 at a CMC-1.2 concentration of 10 ppm. The calcium inhibition results are tabulated in Table 12.

TABLE 12

Scale inhibition of 1.2 DS carboxymethyl cellulose(CMC-1.2) at different molecular weights

| Amount of 30% H2O2 added to 100 gm of solution | Weight average molecular weight, Mw | Number average molecular weight, Mn | % Calcium carbonate inhibition at polymer concentration dosage of 10 ppm |
|---|---|---|---|
| 0 gm | 550,000 | 57,500 | 63.3 |
| 0.5 gm | 13,200 | 7,420 | 77.6 |
| 1.5 gm | 6,400 | 4,240 | 65.3 |
| 5.0 gm | 3,590 | 2,770 | 36.7 |

What is claimed is:

1. A method for inhibiting scale in an aqueous system comprising:
    adding to said aqueous system a depolymerized carboxyalkyl polysaccharide comprising a weight average molecular weight of less than about 500,000 g/mole and a degree of substitution ranging from about 0.5 to about 3 carboxylic groups per sugar unit;
    wherein said polysaccharide is added to the aqueous system in an amount effective to inhibit formation of scale.

2. The method of claim 1 wherein the molecular weight of the carboxyalkyl polysaccharide is reduced through a reaction with oxidizing agents, enzyme reduction, acid reduction, ionizing radiation or electronic beam radiation.

3. The method of claim 1 further comprising adding at least one water treatment agent to the aqueous system.

4. The method of claim 1 wherein the aqueous system comprises oil production systems, cooling systems, boiler systems or general water treatment systems.

5. The method of claim 1 wherein the depolymerized carboxyalkyl polysaccharide is biodegradable.

6. A method for inhibiting scale in an oil or gas production system comprising:
    injecting an aqueous fluid comprising an amount of a depolymerized carboxyalkyl polysaccharide, wherein said polysaccharide has a degree of substitution ranging from about 0.5 to about 3 and a weight average molecular weight of less than about 500,000 g/mole,
further wherein said amount of depolymerized carboxyalkyl polysaccharide is effective to reduce scale downhole.

7. The method of claim 6 wherein the aqueous fluid comprises about 1-500 ppm of the depolymerized carboxyalkyl polysaccharide.

8. The method of claim 7 wherein the aqueous fluid comprises about 5-200 ppm of the depolymerized carboxyalkyl polysaccharide.

9. The method of claim 8 wherein the aqueous fluid comprises about 10-20 ppm of the depolymerized carboxyalkyl polysaccharide.

10. A method of treating scale or corrosion in a subterranean oil or gas well comprising the steps of:
squeezing a scale inhibitor directly into a reservoir section surrounding a well, and then
recycling said scale inhibitor through said well to inhibit scale formation in said well,
wherein the scale inhibitor comprises a depolymerized carboxyalkyl polysaccharide of formula:

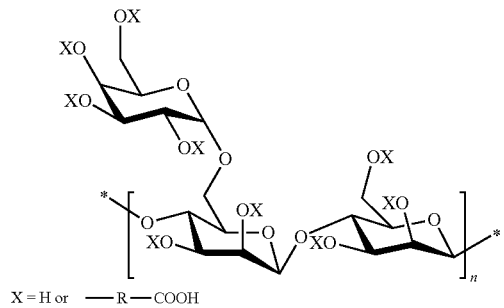

X = H or —R—COOH wherein R comprises:
a linear or branched $C_1$-$C_{22}$ alkyl group, optionally substituted with one or more hetero atoms comprising amine, ether, carboxy, alcohol or thio functionalities; or
a $C_1$ to $C_{22}$ aryl or substituted aryl group; and
further wherein said polysaccharide has a degree of substitution ranging from about 0.5 to about 3 and a weight average molecular weight of less than about 500,000 g/mole.

11. A method for preventing deposition of scale on a surface exposed to process sea water in an oil extraction process that uses sea water, the method comprising the steps of:
supplying process sea water into a rock formation from which oil is to be extracted; and
supplying a scale inhibitor to the process sea water or into the rock formation;
wherein said scale inhibitor prevents deposition of scale comprising calcium or barium salts on the surface exposed to the process sea water, and further wherein the scale inhibitor comprises a compound of formula:

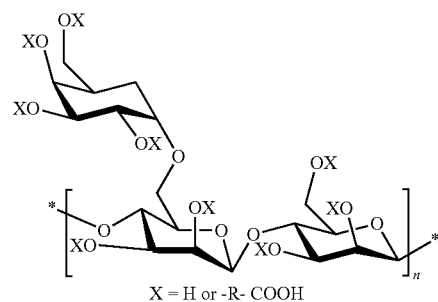

X = H or -R- COOH wherein R comprises:
a linear or branched $C_1$-$C_{22}$ alkyl group, optionally substituted with one or more hetero atoms comprising amine, ether, carboxy, alcohol or thio functionalities; or
a $C_1$ to $C_{22}$ aryl or substituted aryl group; and
further wherein said polysaccharide has a degree of substitution ranging from about 0.5 to about 3 and a weight average molecular weight of less than about 500,000 g/mole.

12. The method of claim 10, wherein said depolymerized carboxyalkyl polysaccharide is formed by reducing the molecular weight of a carboxyalkyl polysaccharide and depolymerizing said carboxyalkyl polysaccharide.

13. The method of claim 1, wherein the depolymerized carboxyalkyl polysaccharide comprises guar.

14. The method of claim 6, wherein the depolymerized carboxyalkyl polysaccharide comprises guar.

15. The method of claim 1, wherein the degree of substitution ranges from 1.6 to about 3.

16. The method of claim 15, wherein the degree of substitution is 1.6.

17. The method of claim 6, wherein the degree of substitution ranges from 1.6 to about 3.

18. The method of claim 10, wherein the degree of substitution ranges from 1.6 to about 3.

19. The method of claim 11, wherein the degree of substitution ranges from 1.6 to about 3.

20. The method of claim 1, wherein the amount of polysaccharide ranges from about 5 ppm to about 200 ppm.

21. The method of claim 1, wherein the amount of polysaccharide ranges from about 10 ppm to about 250 ppm.

22. The method of claim 6, wherein the amount of polysaccharide ranges from about 10 ppm to about 250 ppm.

23. The method of claim 10, wherein the amount of polysaccharide ranges from about 5 ppm to about 200 ppm.

24. The method of claim 10, wherein the amount of polysaccharide ranges from about 10 ppm to about 250 ppm.

25. The method of claim 11, wherein the amount of polysaccharide ranges from about 5 ppm to about 200 ppm.

26. The method of claim 11, wherein the amount of polysaccharide ranges from about 10 ppm to about 250 ppm.

27. The method of claim 1, wherein scale inhibition in said aqueous system is maintained at a percent inhibition of greater than about 60%.

* * * * *